United States Patent [19]
Pellet

[11] Patent Number: 5,744,667
[45] Date of Patent: Apr. 28, 1998

[54] PREPARATION OF TRIMETHYL PENTANES BY HYDROGEN TRANSFER

[75] Inventor: Regis J. Pellet, Croton-on-Hudson, N.Y.

[73] Assignee: Texaco Inc., White Plains, N.Y.

[21] Appl. No.: 775,322

[22] Filed: Dec. 31, 1996

Related U.S. Application Data

[60] Provisional application No. 60/009,473 Dec. 28, 1995.
[51] Int. Cl.$^6$ ..................................................... C07C 5/02
[52] U.S. Cl. .......................... 585/257; 585/250; 585/700; 585/709; 585/721; 585/722; 585/656
[58] Field of Search ............................... 585/250, 257, 585/700, 709, 721, 722, 656

[56] References Cited

U.S. PATENT DOCUMENTS

| | | | |
|---|---|---|---|
| 3,692,863 | 9/1972 | Kmecak et al. | 585/257 |
| 5,227,552 | 7/1993 | Chang et al. | 585/257 |
| 5,227,569 | 7/1993 | O'Young et al. | 585/671 |
| 5,326,922 | 7/1994 | Huss, Jr. et al. | 585/722 |
| 5,545,388 | 8/1996 | Rogers et al. | 585/642 |

*Primary Examiner*—Elizabeth D. Wood
*Attorney, Agent, or Firm*—Henry H. Gibson; Carl G. Ries

[57] ABSTRACT

Gasoline range olefins such as trimethyl pentene are saturated to the corresponding paraffins such as trimethylpentane by hydrogen transfer from lower molecular weight paraffins using a catalyst comprising platinum supported on a large pore borosilicate zeolite which has been partially neutralized by the addition of alkali cations.

4 Claims, No Drawings

PREPARATION OF TRIMETHYL PENTANES BY HYDROGEN TRANSFER

This application is a continuation-in-part of copending Pellet U.S. Patent application Ser. No. 60/009,473 filed Dec. 28, 1995, and entitled "NOVEL ROUTE TO TRIMETHYLPENTANES TRANSFER HYDROGENATION" now abandoned.

BACKGROUND OF THE INVENTION

1. Technical Field of the Invention

This invention relates to a process wherein gasoline range olefins are saturated to the corresponding paraffins by hydrogen transfer from lower molecular weight paraffins. More particularly, the present invention relates to the saturation of gasoline range olefins using novel catalysts comprising platinum supported on large pore borosilicate zeolites which have been partially neutralized by the addition of alkali cations.

2. Prior Art

Palladium has been used to catalyze intermolecular hydrogen transfer in 1-hexene to form hexane and hexadiene (Proc 5th Int. Cong. Catal., paper 53, 783, 1973). A conversion of about 4 to 7% was observed at 200° C. in a one hour batch reaction. When $C_{14}$ or $C_{17}$ paraffins were added to the 1-hexene feed, no hydrogen transfer was observed from the added paraffin to the hexene while the intermolecular transfer continued as if the added paraffin were absent. The study concluded that strong olefin absorption prevented the paraffin from absorbing and undergoing cross hydrogen transfer.

U.S. Pat. No. 3,321,545 describes the use of chromia on alumina to saturate ethylene or propylene with hydrogen from higher molecular weight paraffins. According to the examples presented, low reactivity was partially overcome by the use of extremely slow feed rates (150 v/v/hr) and relatively high reaction temperatures (800° F.).

U.S. Pat. No. 4,433,190 discloses a process for converting an alkane such as n-butane to dehydrogenated and isomerized products using a catalyst comprising a crystalline borosilicate containing a nobel metal. There is no disclosure or indication that boron containing zeolites are particularly effective components for hydrogen transfer processes or that partial alkali exchange would render them even more effective for hydrogen transfer.

In U.S. Pat. No. 4,438,288 there is disclosed a dehydrogenation process using a catalyst comprising a platinum group component, an alkali or alkaline earth component and a porous support material. There is no disclosure that zeolites, boron substituted zeolites or boron substituted zeolites partially exchanged with alkali metals would be effective in hydrogen transfer between olefins and paraffins.

A process for hydrogenating alkenes in the presence of alkanes and a heterogeneous catalyst is disclosed in U.S. Pat. No. 5,227,552. The patent teaches that the process is useful for hydrogenating olefinic streams produced in a number of petroleum refining operations for the purpose of producing high octane paraffinic gasoline blending components. A large excess of paraffin is required in order to effect the hydrogenation of olefins. Paraffins are provided only as a source of hydrogen and little paraffin conversion to the corresponding olefin is observed. Extremely low olefinic feed rates are required in order to achieve moderate conversions. The patent discloses the use of metal components (palladium is preferred) and the use of low acidity medium and large pore zeolites such as palladium on zeolite beta and palladium on cation exchanged zeolite beta. The cations used to prepare the exchanged beta zeolite include cerium and barium.

BACKGROUND INFORMATION

Regulatory developments have lead refiners to seek methods for reformulating motor fuels to meet increasingly stringent air quality requirements. One approach is to reduce fuel olefin content while increasing the relative content of high octane isoparaffins (alkylate). Typically the production of alkylate requires the availability of butenes. The need to reduce the olefin content of potential fuels places an ever increasing demand on available refinery hydrogen in order to effect saturation.

In general terms, it can be said that regulations have placed two opposing demands on the refiner. One is the need to remove hydrogen from hydrocarbon precursors in order to generate oxygenates and alkylate; the second is the need to add hydrogen to unsaturates present in fuels such as gasoline. Conventional technologies to add or remove hydrogen have their limitations.

SUMMARY OF THE INVENTION

This invention relates to a process wherein gasoline range olefins are saturated to the corresponding paraffins by hydrogen transfer from lower molecular weight paraffins. More particularly the present invention relates to the saturation of gasoline range olefins using novel catalysts comprising platinum supported on large pore borosilicate zeolites which have been partially neutralized by the addition of alkali cations.

In accordance with one embodiment of the present invention, a method for the production of trimethylpentanes is provided which comprises the steps of:

a) dimerizing mixed butenes in the presence of a Y zeolite at a temperature of about 100° to about 150° C. to form a $C_8$ olefin reaction product containing a predominant amount of trimethyl pentenes, and b) reacting butane with the butene dimers in the $C_8$ olefin reaction product in the presence of a hydrogen transfer catalyst comprising platinum supported on a partially neutralized zeolite at a temperature of about 150° to about 450° C.

DETAILED DESCRIPTION OF THE PRESENT INVENTION

It has been found, in accordance with the present invention, that gasoline range olefins can be saturated to form the corresponding paraffin by hydrogen transfer from lower molecular weight paraffins. The process is effectively catalyzed by platinum which is supported on a large pore borosilicate zeolite which has been treated with alkali to repress acid catalyzed reactions. Boron beta zeolite which has been neutralized with lithium cation is particularly effective.

Catalyst platinum content can range from 0.1% up to 2 weight percent. Zeolites effective for the present invention are selected from those zeolites which have a large pore structure and which contain boron as a component of the zeolite crystal structure. The zeolite boron content should be chosen to be equal to or greater than the catalyst platinum content on a molar basis and should be selected from the range 0.05 to 2 weight percent as boron. Zeolites which are particularly effective are low in aluminum content. Effective zeolites have aluminum contents below 0.5 weight percent as aluminum. Catalyst of the present invention will contain sufficient alkali to effectively neutralize all acidity associated with the zeolite's aluminum content. Accordingly, catalysts of the present invention will contain alkali in excess of the zeolite base's aluminum content on a molar basis. Neutralization of the weak acidity associated with zeolitic boron is not required in order to obtain the benefits of the present invention. Catalysts of the present invention can be used as powders. More preferably, catalysts will be bound and formed into extrudates, pills or beads before used in the process of the present invention. Methods of binding currently used to prepare commercial catalysts are acceptable. Acceptable binders include but are not limited to silica, alumina and clays. Binders are selected so as not to introduce acidity into the catalyst.

The process of the present invention may be conducted at temperatures ranging from 150° C. to 500° C. and more preferably from 300° to 400° C. The process is conducted at pressures which may range from 0 to 300 psig, more preferably from 0 to 100 psig. The feed will consist of a mixture of a paraffin and olefin. Olefins are typically, but not limited to gasoline olefins which typically can include $C_5$ through $C_{10}$ olefins. Paraffins can be selected from the same molecular weight range but are preferably selected from a lighter molecular weight range including $C_3$ and $C_4$ paraffins. Feed paraffin to olefin ratios can range from 1 to 100, preferably from 3 to 10. Feed weight hourly space velocity can range from 1 to 20, preferably from 1 to 10.

EXAMPLES

In order to demonstrate the surprising features of the present invention, a carbon catalyst and a number of zeolite-based catalysts were prepared. In general, the zeolite catalysts were prepared by pore-filling the hydrogen form of the zeolite with a solutions containing platinum or platinum and lithium salts. A steam stabilized Y zeolite-based catalyst was prepared in a similar fashion except that the zeolite was aluminum bound before pore-filling.

Description of Catalyst Base Materials

A commercially prepared activated wood carbon, offered as Nuchar BX-7530 was used as a comparative catalysts as received from Westvaco Chemicals as a powder.

The aluminosilicate, Beta and the borosilicate, boron-Beta (B-Beta) were obtained from PQ Corporation. These zeolites were obtained in the as-synthesized form containing tetraethylammonium cation and were calcined at 550° C. in air to remove this template and to render these zeolites in the hydrogen form. The borosilicate was analyzed to contain 42.3% silicon, 1.05% boron and only 0.1% aluminum after calcination. The aluminosilicate, beta was found to contain no boron and a much higher aluminum content.

A steam stabilized Y zeolite catalyst base was prepared using Y-82 zeolite powder obtained from Union Carbide Corporation. Alumina bound Y-82 extrudates were prepared by mixing zeolite powder with alumina sol (20% $Al_2O_3$ by weight). The mixture was stirred until homogeneous and then gelled by the addition of a small amount of ammonium hydroxide. The resultant paste was extruded to form 1/16" extrudates which were dried at 120° C. overnight and calcined at 600° C. for 4 hours.

Platinum and Alkali Loaded Zeolite Based Catalysts

A catalyst of the present invention as well as comparative catalysts were prepared using the zeolites described above by pore filling with platinum and alkali containing components. The procedure used in each preparation was similar. All catalysts were prepared to contain about 0.6% platinum but were prepared to contain varying amounts of the alkali, lithium. A catalyst of the present invention was prepared as follows. A platinum and lithium loaded powder was prepared by mixing about 2.95 grams of Boron-Beta zeolite powder prepared as above with about 1.8 grams of a first stock solution containing 0.1912 grams of tetraamine platinum chloride in 10.53 grams of deionized water and 7.33 grams of a second stock solution containing 0.8004 grams of lithium carbonate in 86.77 grams of deionized water. To this slurry, an additional 6.63 grams of deionized water were added and the resulting mixture was pH adjusted to 10 then partially dried under vacuum with stirring at 130° C. and then dried overnight at 120° C. under air. The dried, pore filled powder was calcined at 300° C. under air for 4 hours. This catalyst was prepared to contain 0.6% platinum, 0.42% lithium and represents a catalyst of the present invention. In a similar manner, several comparative catalysts were prepared. The compositions of all catalysts used in the following examples is provided in Table 1, below:

TABLE I

| Example | Example Type | Catalyst Description | Platinum Content | Lithium Content |
|---------|--------------|----------------------|------------------|-----------------|
| 1 | Comparative[1] | Nuchar Carbon | 0 | 0 |
| 2 | Comparative[2] | Beta | 0.6 | 1.04 |
| 3 | Comparative[3] | Steamed Y | 0.6 | 0 |
| 4 | Comparative[4] | Boron-Beta | 0.6 | 0 |
| 5 | Invention[5] | Boron-Beta | 0.61 | 0.42 |

[1]Catalyst was in the form of a powder
[2]Catalyst was in the form of a zeolite powder
[3]Catalyst was in the form of an alumina powder
[4]Catalyst was in the form of a zeolite powder
[5]Catalyst was in the form of a zeolite powder

CATALYST EVALUATION

The catalysts of the present invention are surprisingly active and selective for the production of trimethylpentane and butenes from a mixture of diisobutene and butanes. Specifically, catalysts containing a platinum component supported on a partially neutralized Boron-Beta zeolite exhibit superior performance when compared to prior art catalysts as well as catalyst prepared using un-neutralized catalysts. In order to demonstrate this surprising advantage, all catalysts described above were evaluated as follows. Each catalyst was ground to pass a 20 mesh screen (U.S. Sieve Series) and 0.30 grams were loaded to a tubular reactor (0.25 inches I.D.) The catalyst bed temperature was ramped to 550° C. in hydrogen over a period of one hour and maintained at 550° C. for one half hour to remove volatile components and moisture if any and to reduce the platinum component. After this activation, the catalyst was cooled to 350° C. and a mixed feed containing about 88% butanes (either n-butane or isobutane) and 12% di-isobutene was passed over the catalyst at one atmosphere pressure. The diisobutene flow rate was about 0.9 grams per gram of catalyst per hour while the butanes flow rate was, typically about 6.9 grams per gram of catalyst per hour. The reactor effluent was periodically analyzed by an on-line gas chromatograph capable of separating key products formed. The results of this analysis are summarized in Table II.

As can be seen from the table, all catalysts are active for trimethylpentene conversion. However, with the comparative catalysts based on carbon, zeolite beta and zeolite Y (Examples 1, 2, and 3), the main products of trimethylpentene conversion are butenes and non-$C_4$, non-$C_8$ products. There is little saturation of trimethylpentene to form the desired trimethylpentane. From the table, the Boron-beta-based catalyst which has not been acid neutralized with lithium (Example 4) shows very similar performance to the comparative examples with little trimethylpentane production. Only the catalyst of the present invention, which is prepared from the borosilicate B-beta and is neutralized with lithium exhibits substantial production of trimethylpentane with a 45% yield.

TABLE II

| Example Number | 1 | 2 | 3 | 4 | 5 |
| --- | --- | --- | --- | --- | --- |
| Catalyst | Carbon | Pt on Li Beta | Pt on Steamed Y | Pt on B-Beta | Pt on Li B-Beta |
| Run Temperature | 350 | 350 | 150 | 350 | 350 |
| Run Pressure (psig) | 0 | 0 | 0 | 0 | 0 |
| Feed Paraffin | isobutane | n-butane | isobutane | n-butane | n-butane |
| Feed Olefin | trimethylpentene | trimethylpentene | trimethylpentene | trimethylpentene | trimethylpentene |
| Feed Paraffin/Olefin Ratio, g/g | 7.58 | 7.05 | 7.58 | 7.05 | 7.05 |
| Feed Flow Rate (WHSV) | 6.9 | 7.7 | 6.9 | 7.7 | 7.7 |
| Trimethylpentene Conversion | 29.40% | 99.70% | 95.10% | 100.00% | 85.85% |
| Trimethylpentane Yield | 3.40% | 0.70% | 13.20% | 1.13% | 45.35% |
| Butene Yield | 23.80% | 75.20% | 75.00% | 89.22% | 35.29% |
| Non C4 + Non C8 Products | 2.20% | 23.80% | 6.96% | 10.78% | 5.21% |

These examples show the surprising and superior performance of catalyst of the present invention for saturation of gasoline range olefins using light paraffins as hydrogen source.

I claim:

1. A method for producing a product paraffin having from 5 to 10 carbon atoms from a reaction mixture containing:
   a) an acceptor olefin containing 5 to 10 carbon atoms and having the carbon backbone structure of said selected paraffin, and
   b) a donor paraffin containing 3 to 10 carbon atoms and having a carbon backbone structure different from that of said selected paraffin; which process comprises contacting said reaction mixture with a heterogeneous catalyst comprising platinum supported on a lithium neutralized large pore boron beta zeolite containing from 0.1% up to 2 wt. % of platinum and 0.05 to 2 wt. % of boron under conditions effective to dehydrogenate at least a portion of said donor paraffin and to form said product paraffin.

2. A method for the production of trimethyl pentanes which comprises reacting butane with trimethyl pentene in the presence of a hydrogen transfer catalyst comprising platinum supported on a lithium neutralized large pore boron beta zeolite at a temperature of about 120° to about 450° C., said catalyst containing from 0.1% up to 2 wt. % of platinum and 0.05 to 2 wt. % of boron.

3. A method as in claim 2 wherein the lithium neutralized large pore boron-beta zeolite containing about 2 wt. % of boron and less than 0.5 wt. % of aluminum.

4. A method as in claim 3 wherein:
   a. butenes are dimerized in the presence of a Y zeolite at a temperature of about 100° to about 150° C. to form a $C_8$ olefin reaction product containing trimethyl pentenes, and
   b. the $C_8$ olefin reaction product is reacted with butane at a temperature of about 150° to about 450° C. in the presence of a catalyst comprising platinum supported on a lithium neutralized boron beta zeolite.

* * * * *